United States Patent
Ferber et al.

(10) Patent No.: US 6,760,945 B2
(45) Date of Patent: Jul. 13, 2004

(54) ACOUSTIC TOOTHBRUSH

(75) Inventors: Roman S. Ferber, West Bloomfield, MI (US); Edmund L. Sokolik, Ann Arbor, MI (US)

(73) Assignee: HoMedics, Inc., Commerce Township, MI (US)

( * ) Notice: Subject to any disclaimer, the term of this patent is extended or adjusted under 35 U.S.C. 154(b) by 241 days.

(21) Appl. No.: 10/047,333

(22) Filed: Jan. 14, 2002

(65) Prior Publication Data

US 2002/0092104 A1 Jul. 18, 2002

Related U.S. Application Data

(60) Provisional application No. 60/261,720, filed on Jan. 12, 2001.

(51) Int. Cl.⁷ .......................... A46B 13/00; A61C 17/16
(52) U.S. Cl. ......................................... 15/22.2; 15/22.1
(58) Field of Search ................................ 15/22.1, 22.2, 15/28, 22.4, 21.1

(56) References Cited

U.S. PATENT DOCUMENTS

| | | |
|---|---|---|
| 5,165,131 A | 11/1992 | Staar |
| 5,263,218 A | 11/1993 | Giuliani et al. |
| 5,311,632 A | 5/1994 | Center |
| 5,311,633 A | 5/1994 | Herzog et al. |
| 5,343,883 A | 9/1994 | Murayama |
| 5,369,831 A | 12/1994 | Bock |
| 5,378,153 A | 1/1995 | Giuliani et al. |
| 5,546,624 A | 8/1996 | Bock |
| 5,613,259 A | 3/1997 | Craft et al. |
| RE35,712 E | 1/1998 | Murayama |
| 5,784,742 A * | 7/1998 | Giuliani et al. .............. 15/22.1 |
| 5,934,908 A | 8/1999 | Woog et al. |

* cited by examiner

Primary Examiner—Robert J. Warden, Sr.
Assistant Examiner—Laura C Cole
(74) Attorney, Agent, or Firm—Brooks Kushman P.C.

(57) ABSTRACT

An electric toothbrush having a detachable brush head assembly including a driven shaft that is driven by a driveshaft disposed with in a housing. The driveshaft is part of or secured to a torsion bar that supports an armature including a pair of magnets. An electric coil receives an alternating flow of current at a predetermined frequency that causes the magnets to be alternately attracted to the coil and causes the torsion bar to oscillate in an oscillatory rotary motion.

23 Claims, 7 Drawing Sheets

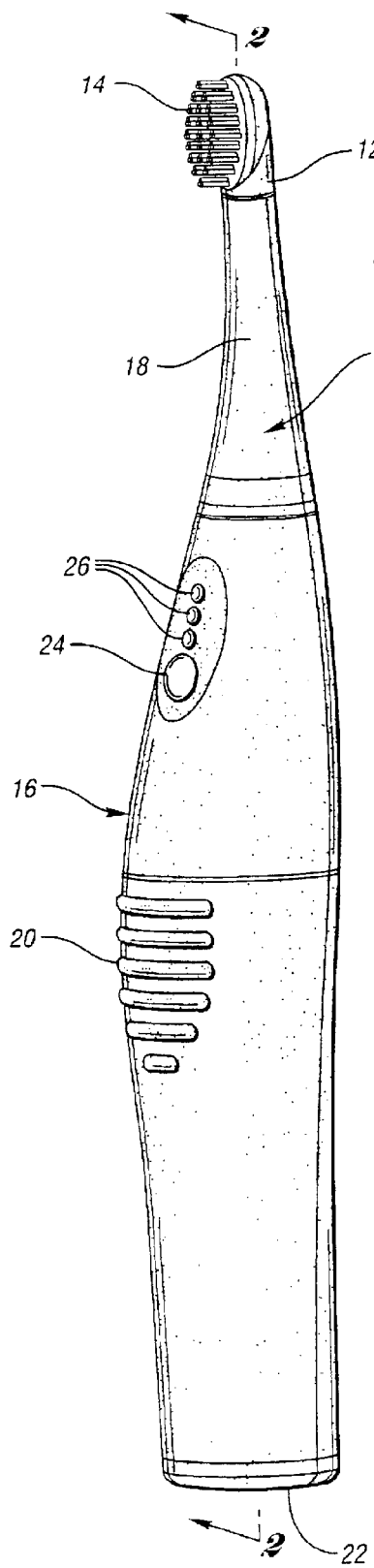
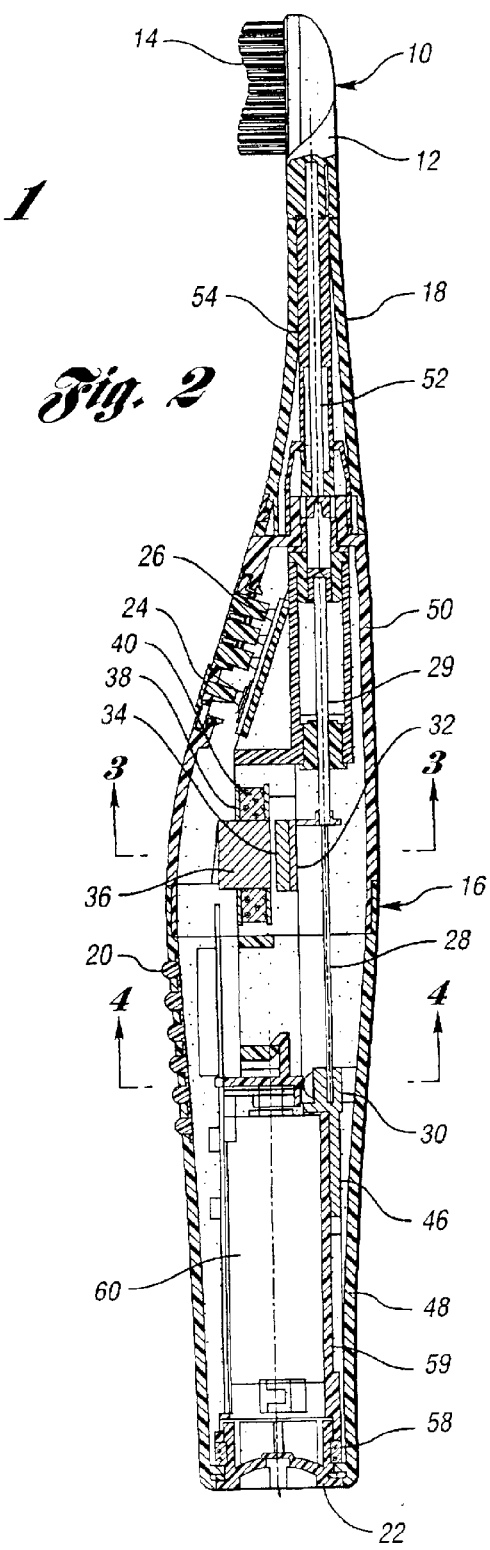
Fig. 1
Fig. 2

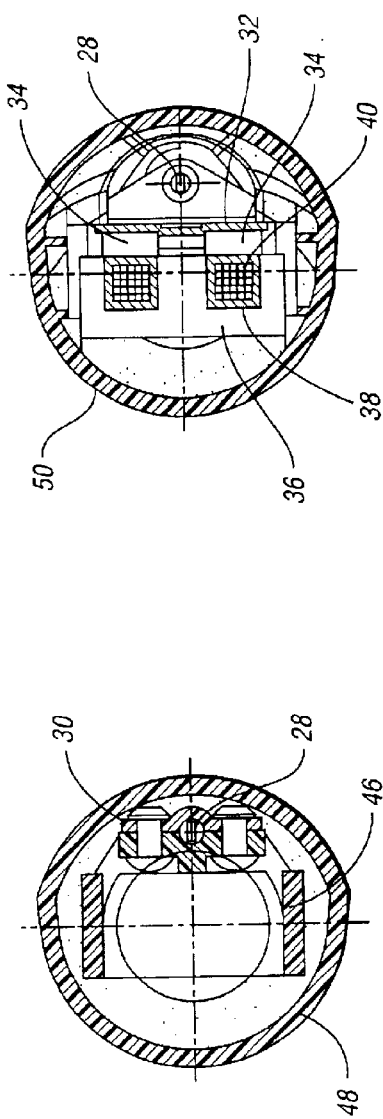
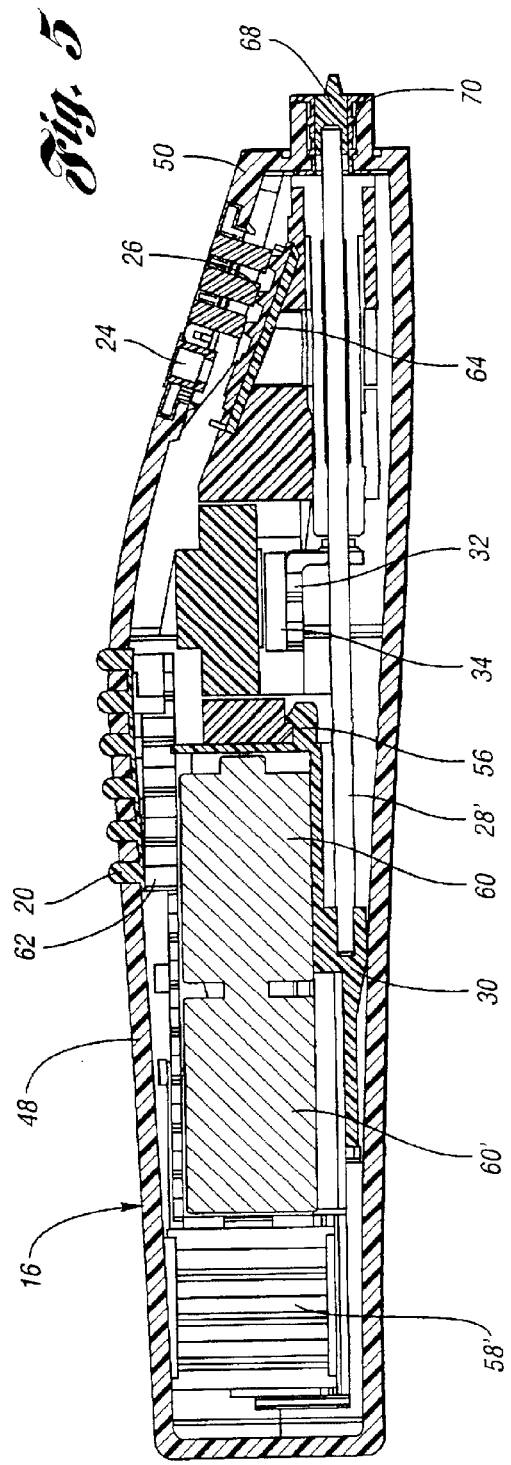

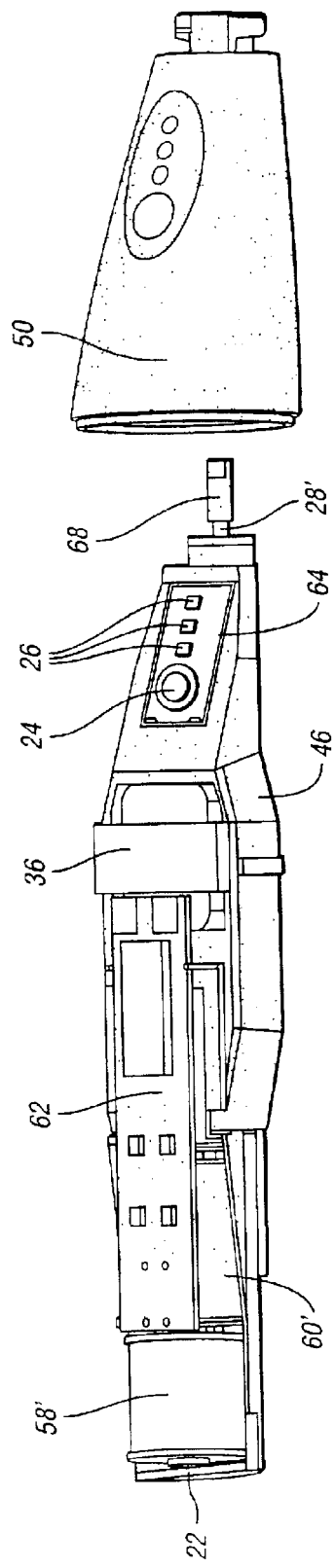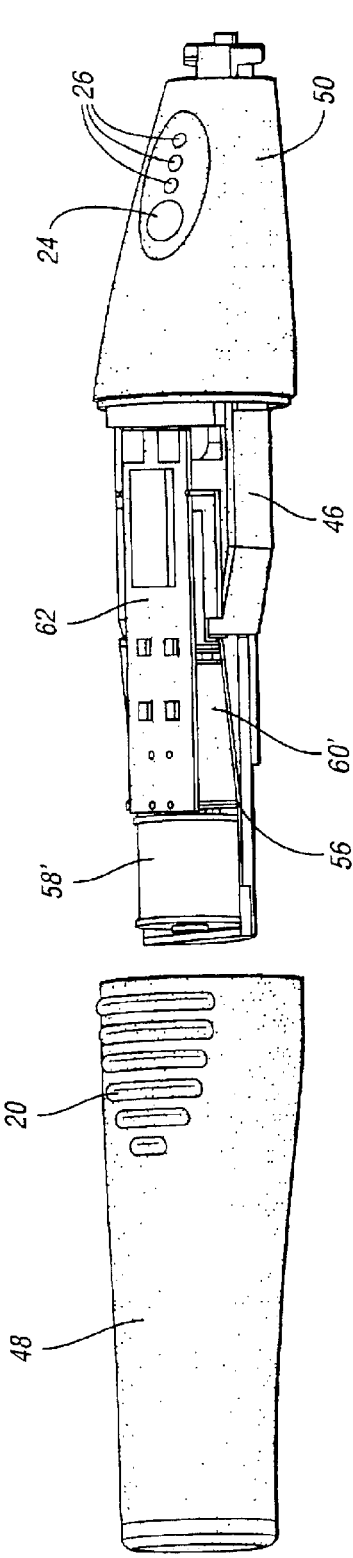

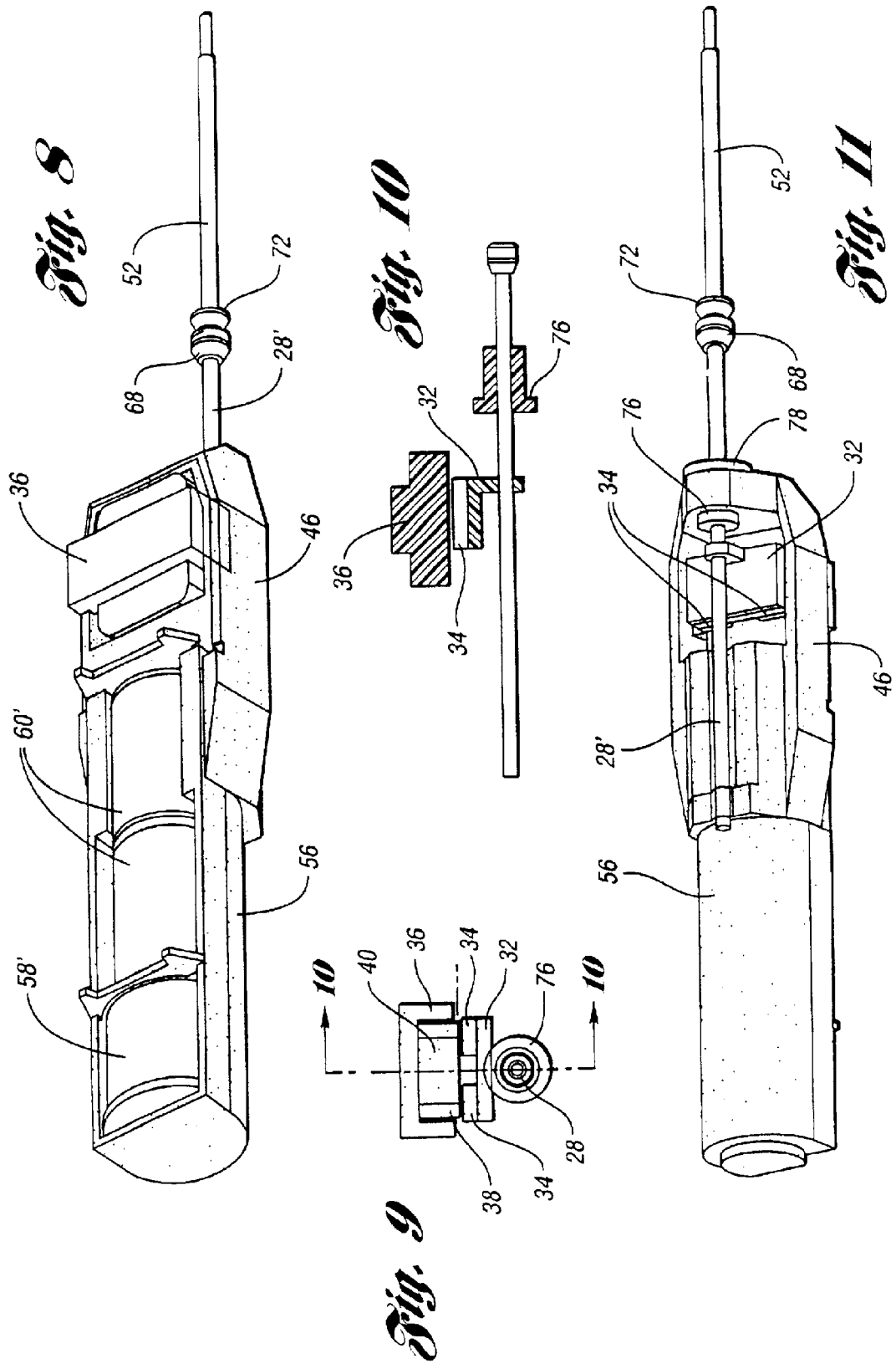

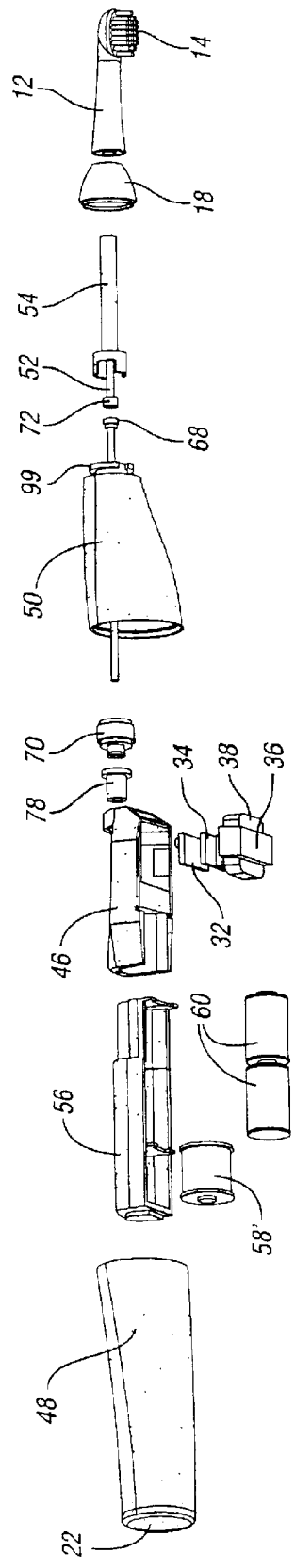
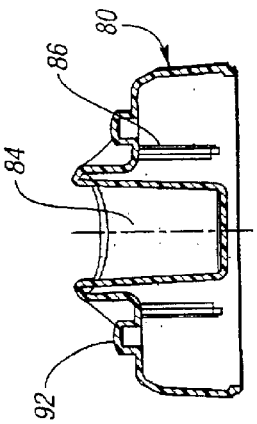
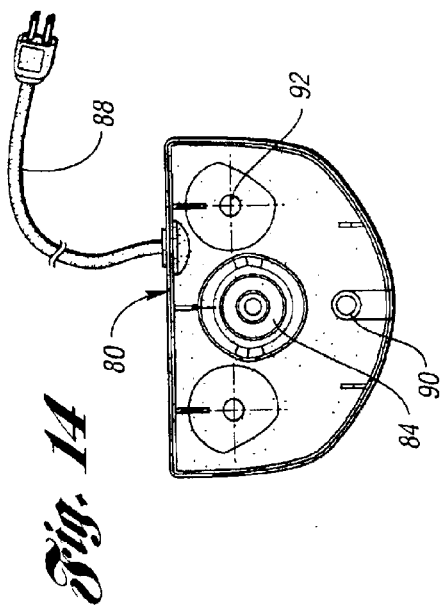
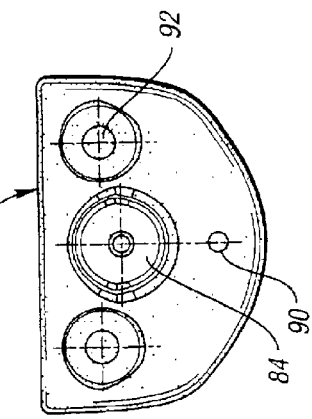

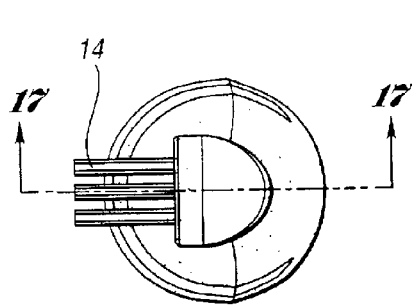
*Fig. 16*
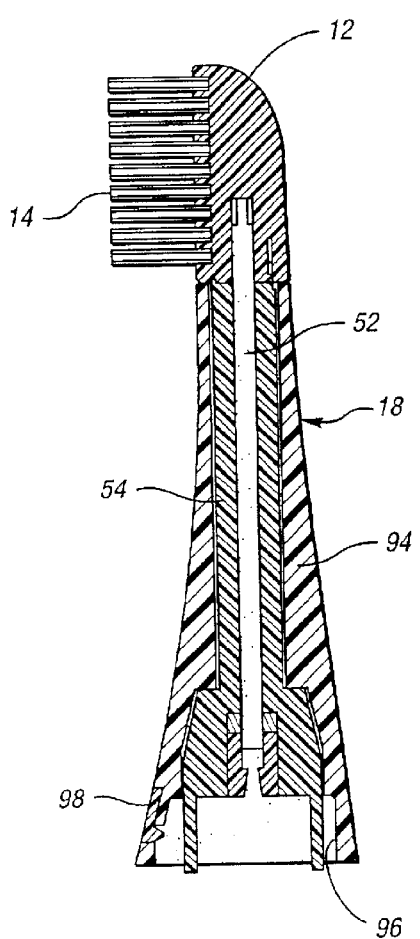
*Fig. 17*
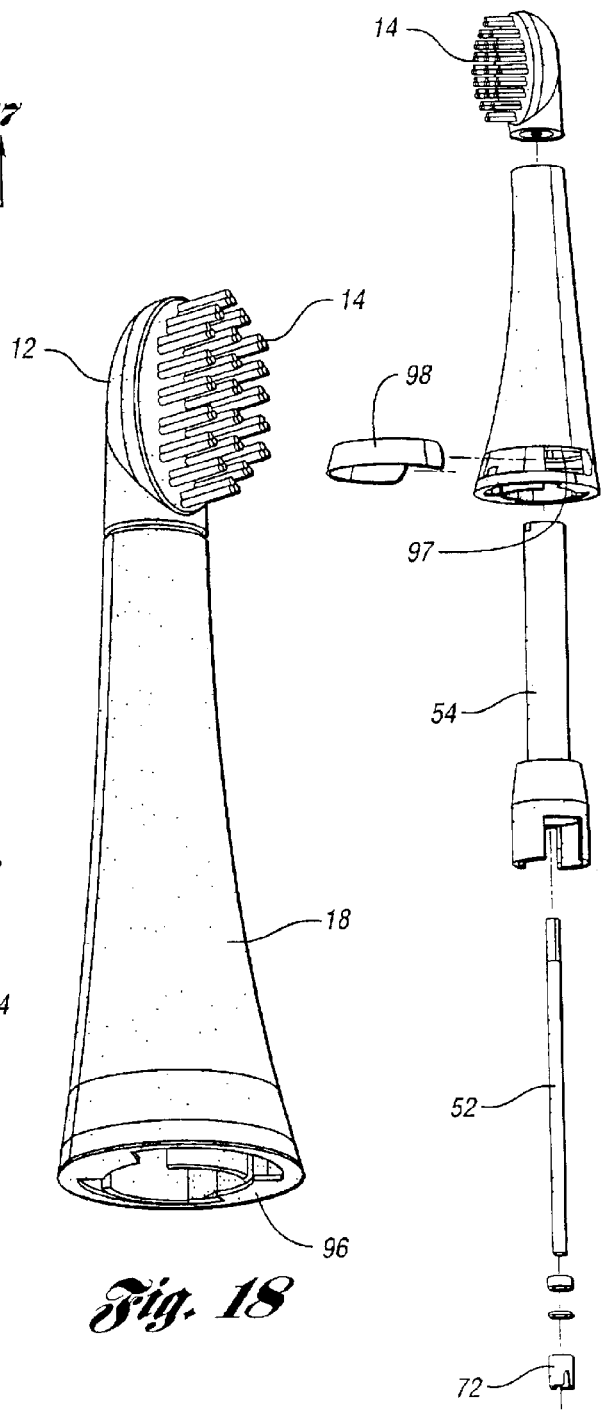
*Fig. 18*
*Fig. 19*

ACOUSTIC TOOTHBRUSH

CROSS-REFERENCE TO RELATED APPLICATIONS

This application claims the benefit of U.S. provisional application Serial No. 60/261,720 filed Jan. 12, 2001.

BACKGROUND OF THE INVENTION

1. Field of the Invention

The present invention relates to an a sonic toothbrush appliance and charging base.

2. Background Art

Power-operated toothbrushes have long been used to make the task of toothbrushing easier and more convenient. Older power toothbrushes required excessive movement of the brush head to obtain effective cleaning. Excessive movement of the brush head could potentially injure the gums and soft palette of a user.

Ultrasonic toothbrushes have been developed that move a toothbrush head reciprocally or in an oscillating path by means of a rotating linkage or other drive mechanism. One example of an ultrasonic toothbrush is disclosed in U.S. Pat. No. 5,378,153 to Giuliani et al. The Giuliani patent specifies a bristle tip velocity in excess of 1.5 meters per second (m/s) that is extremely vigorous and may be excessive for some individuals.

Products made in accordance with the Giuliani patent may also utilize a brushing head that requires two expensive rare earth magnets on the replaceable brush component that must be thrown away when the brush head is replaced. The use of rare earth magnets on a replaceable component unnecessarily adds to the cost of the replaceable brush element. The extremely high loading necessitated by the geometry of the torsion bar used in the Giuliani device requires that it be made of an expensive alloy such as beryllium-copper-titanium. The torsion bar is also disposed of when the brush head is replaced adding considerable cost to the replacement brush.

Further, user assembled component parts of the Giuliani patent include critical components that require maintaining spacing between parts that are assembled by the user. The brush head is a user assembled part that is disposable and must often be replaced. If anything sticks to the magnets of the disposable brush head, it can cause rubbing or contact problems. The Giuliani device is also sensitive to dirt, mis-handling, improper installation, manufacturing problems, and product variation from required manufacturing tolerances. If there are changes in the manufacturing standards for a brush head, the brush head may not work with an older toothbrush drive due to the arrangement of the critical components in the Giuliani product.

These and other problems and disadvantages associated with prior art power toothbrushes are addressed by Applicant's invention that provides a sonic toothbrush that operates at a safe and effective level while allowing for the use of a low cost replaceable brush head that is easy for a user to replace and does not require the user to assemble critical parts having close tolerance requirements.

SUMMARY OF THE INVENTION

According to the present invention, a sonic toothbrush is provided that features a replaceable toothbrush head that is driven by a torsion bar that is anchored at one end and moved in an arcuate rotary motion about the brush shaft axis. The motion closely approximates the brush action recommended by the American Dental Association. Rotary movement of the torsion bar is generated by providing an electromagnet on a core in the handle of the toothbrush that acts upon a pair of magnets secured to a magnet plate that is in turn secured to the torsion bar that is fixed at one end to the handle.

According to one aspect of the invention, an electric toothbrush is provided that includes a brush head assembly, a housing, and a frame enclosed by the housing. A power supply is contained within the housing and an electric coil is secured to the frame and electrically connected to the power supply through a control circuit that creates an alternating flow of current in the coil. The brush head assembly is connected to a distal end of an elongated shaft. The elongated shaft has an internal end that is disposed within the housing. A torsion bar is secured to the frame at the first end. An armature is connected to a second end of the torsion bar and the internal end of the elongated shaft. First and second magnets are arranged on the armature. The magnets are in line generally in a plane that is parallel to a central access of the shaft. The alternating flow of current in the electric coil alternates at a predetermined frequency to cause the magnets to be alternately attracted to the coil thereby causing the torsion bar to twist and the shaft to oscillate in the desired oscillatory rotary motion.

According to another aspect of the invention, the frame is a one piece die casting to which the coil, torsion bar and bearing journaling the internal end of the shaft are secured. A torsion bar is preferably clamped by an anchoring plate to the frame at its first end. A bearing journals one end of the elongated shaft for oscillating rotary movement and inhibits translation movement.

According to another aspect of the invention, the brush head assembly is supported on a detachable shaft that is detachable from the elongated shaft. Further, the brush head assembly may be detached from the elongated shaft without opening the housing and without affecting the coil and magnets.

According to yet another aspect of the invention, the torsion bar is secured to the armature between the first and second magnets. The elongated shaft is connected at its internal end to the armature. The armature supporting the first and second magnets has a flat plate portion on which the first and second magnets are disposed and a flange extending perpendicularly relative to the flat plate portion. The elongated shaft is secured to the flange. The coil may be formed on an e-shaped coil armature.

According to a further aspect of the invention, a charging coil is contained within the housing for recharging the power supply contained in the housing. The toothbrush may be provided in combination with a charging base wherein a charging circuit is provided to charge the batteries and wherein placing the electric toothbrush in the base ends an operating cycle of the toothbrush.

According to another aspect of the invention, the toothbrush may have a single control switch that is depressed multiple times to select one of a plurality of operational speeds. A plurality of LEDs are used to indicate the speed of the brush operation.

According to another aspect of the invention, an electric toothbrush is provided that includes a handle enclosing an electric coil that oscillates the driveshaft about a longitudinal axis. The driveshaft may be formed in one or two pieces. If it is formed in one piece, the driveshaft is secured to the handle at an inner end and extends through a bearing to a coupler that connects an outer end to a driven shaft that is part of a detachable brush head assembly. The driveshaft may also be formed in two pieces including a torsion bar and a cylindrical shaft that is aligned axially with the torsion bar. The torsion bar is connected on its inner end to the handle and is connected at its opposite end to the cylindrical shaft. The cylindrical shaft is received in a bearing supported by the handle. A cylindrical shaft pivots arcuately relative to the handle. The brush head assembly is removably secured to the handle. The brush head assembly has a driven shaft that is operatively secured to the cylindrical shaft and is pivoted arcuately by the shaft.

According to another aspect of the invention, the driveshaft is mounted in a bearing having the primary function of eliminating translational motion and allowing primarily only rotary motion.

The sonic toothbrush has multiple amplitude settings and corresponding LED speed indicators. The sonic toothbrush is microprocessor controlled and includes a timer that signals or stops operation of the toothbrush when a predetermined interval of time has passed to assure adequate brushing.

According to the invention, all the critical components of the sonic toothbrush are secured within the handle of the sonic toothbrush so that they are not accessible to the user. The user may change the brush head without opening the handle. The connection between the brush head and the handle is not a close tolerance fit and may be easily performed by a user.

The brush velocity is limited to substantially less than 1.5 meters per second. By limiting the brushing rate, an effective yet comfortable sonic toothbrush is provided with acceptable noise and vibration levels.

BRIEF DESCRIPTION OF THE DRAWINGS

FIG. 1 is a perspective view of a sonic toothbrush made in accordance with the present invention;

FIG. 2 is a cross-sectional view taken along line 2—2 in FIG. 1;

FIG. 3 is a cross-sectional view taken along line 3—3 in FIG. 2;

FIG. 4 is a cross-sectional view taken along line 4—4 in FIG. 2;

FIG. 5 is a partial cross-sectional view similar to FIG. 2 showing the handle of the sonic toothbrush;

FIG. 6 is a partially exploded perspective view of the sonic toothbrush handle shown in FIG. 5;

FIG. 7 is a perspective view of the sonic toothbrush handle having part of the handle housing shown separated from the handle;

FIG. 8 is a perspective view showing the torsion bar movement actuating system;

FIG. 9 is a perspective view showing the coil, magnets and torsion bar;

FIG. 10 is a cross-sectional view taken along the line 10—10 in FIG. 9;

FIG. 11 is a perspective view showing the opposite side of the torsion bar drive compared to that shown in FIG. 8;

FIG. 12 is an exploded perspective view of the sonic toothbrush;

FIG. 13 is a top plan view of the toothbrush holder and charging base;

FIG. 14 is a plan view of the sonic toothbrush base and charging unit;

FIG. 15 is a cross-sectional view of the sonic toothbrush charging base;

FIG. 16 is an end view of the brush head;

FIG. 17 is a cross-sectional view taken along line 17—17 in FIG. 16;

FIG. 18 is a perspective view of the brush head;

FIG. 19 is an exploded perspective view of the brush head and driven shaft that is received within the brush head.

DETAILED DESCRIPTION OF THE PREFERRED EMBODIMENT(S)

Figure 20:
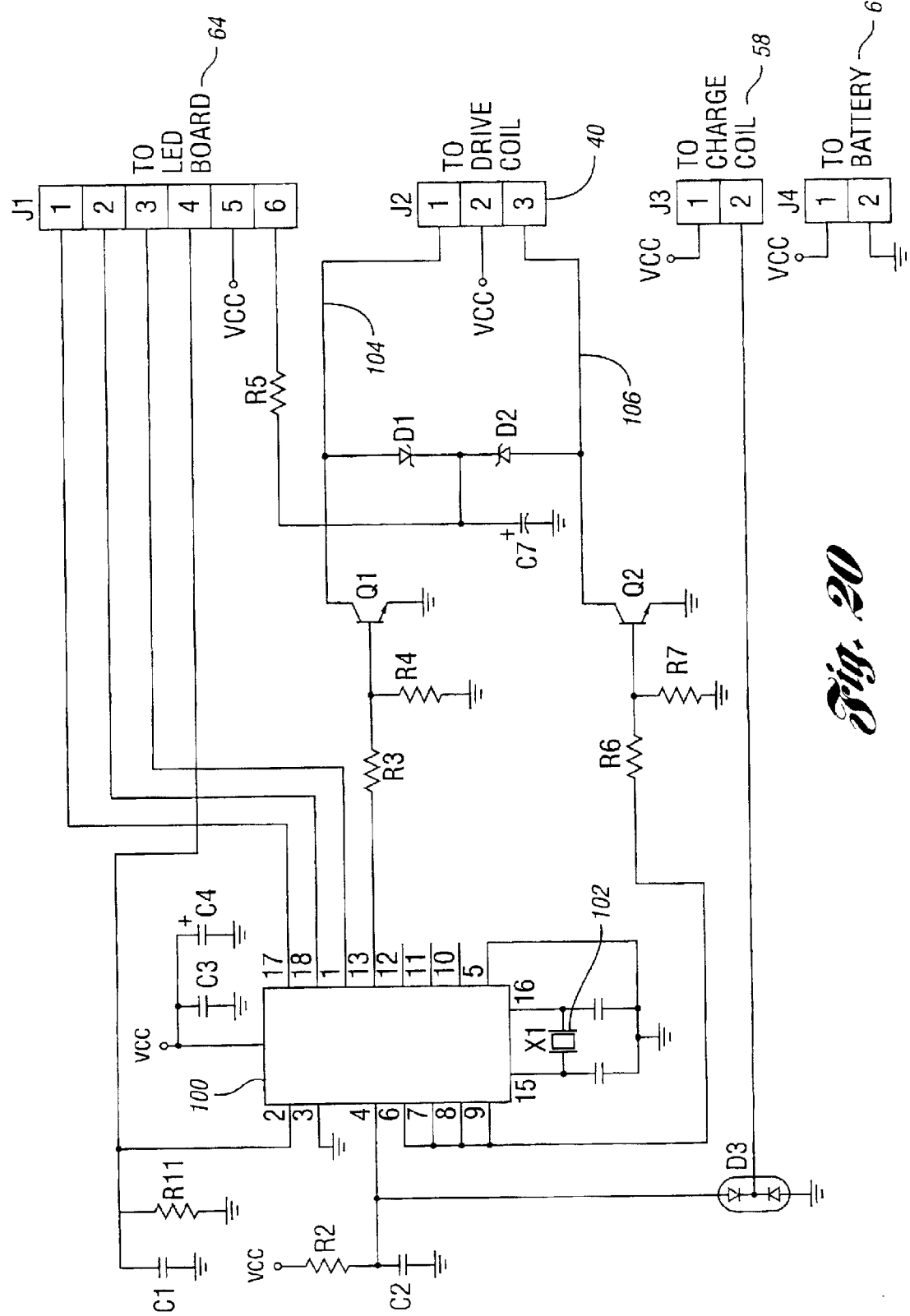
FIG. 20 is an electrical schematic for the sonic toothbrush.

Referring now to FIG. 1, the sonic toothbrush 10 of the present invention is shown to include a brush head 12 having bristles 14 for brushing a person's teeth. The brush head 12 is part of a removable brush head assembly 18 that is received by a brush body housing generally referred to by reference numeral 16. A rubber grip 20 is provided on the housing 16. A battery compartment cover 22 is provided on the lower end of the housing 16. A flex switch 24 is provided to control the speed of operation of the toothbrush 10 and speed indicating LEDs 26 are provided on the housing to indicate the speed of operation as controlled by the flex switch 24.

Referring now to FIGS. 2–4, the sonic toothbrush generally indicated by reference numeral 10 is shown in cross section. A torsion bar 28 is used to drive the brush head 12 so that the bristles 14 are moved in an arcuate path. The torsion bar 28 is received within the housing 16. The torsion bar 28 is connected to an anchoring plate 30 at its lower end as shown in FIG. 2 that holds one end of the torsion bar in a fixed relationship within the housing 16. A magnet plate 32 is provided on the torsion bar 28 at approximately 4 to 5 cm from the anchoring plate 30. The torsion bar is a flat spring that is preferably approximately 2–3 mm in width. A driveshaft 29 is secured on its inner end to the magnet plate 32 and is aligned with the length of the torsion bar 28.

A pair of magnets 34 are provided on the magnet plate 32. The pair of permanent magnets 34 are held in a spaced relationship relative to a core 36 that supports a bobbin frame 38 and bobbin coil 40. Magnets 34 are preferably formed of a high energy material such as Neodymium Iron Boron (NdFeB) alloy or other rare earth or ceramic material. The preferred NdFeB material has a residual induction of about 11,200 Gauss, a coercive force of 10,600 Oersteds and an intrinsic coercive force of over 16,000 Oersteds. The gap between the magnets and the core is about 1.5 mm. The gap allows for bearing wear and manufacturing margin and also has the effect of reducing the brushing amplitude. The bobbin may include 85 turns of No. 28 AWG wire in one embodiment of the invention.

Alternating current provided to the coil 40 causes the pair of magnets 34 to move thereby causing the torsion bar 28 to be twisted to cause driveshaft 29, driven shaft 52, and the brush head 12 to oscillate in a rotary manner about its axis. The alternating flow of current operates at a predetermined frequency of about 250 hz that is at or near the mechanical resonance level that causes mechanical amplification of motion. The bristle tip velocity when tested in air is limited to less than 1.4 meters per second. When the bristle tips are oscillated in a solution of water and toothpaste the bristle tip velocity is reduced because it is operating in a more viscous medium. The torsion bar 28 is secured by the anchoring plate 30 to a frame 46. The core 36 and coil 38 are also secured to the frame 46. The die-cast frame 46 is formed of aluminum or magnesium and provides a common rigid support for the coil 38, core 36, and torsion bar 28.

The brush body housing 16 is divided into a lower housing 48 and a an upper housing 50. The upper and lower housings are preferably formed of ABS. The driveshaft 29 is connected to a driven shaft 52. The driveshaft 29 and driven shaft 52 are preferably formed of stainless steel. The driven shaft 52 is received within a driven shaft holder 54 that is preferably formed of Delrin or other appropriate polymeric material. A charge coil 58 is provided, as shown in FIG. 2, by winding the coil 58 onto a battery compartment 59. The charge coil 58 charges a battery 60.

As shown in FIG. 5, an alternative embodiment is shown in which a cylindrical driveshaft/torsion bar 28' extends from the anchoring plate 30 to the driven shaft 52.

Referring now to FIGS. 5–12, the operating system is shown in greater detail. An alternative charge coil 58' is housed within the brush body housing 16 that is used to charge a pair of rechargeable batteries 60'.

The main circuit board 62 is secured within the brush body housing 16 and includes many of the components described in the circuit of FIG. 20 that will be described subsequently. A switch and LED circuit board 64 is provided in conjunction with the flex switch 24 and speed indicating LEDs 26.

A coupler 68 is provided on the end of the driveshaft/torsion bar 28' or driveshaft 29. A bearing 70 is provided to limit the movement of the driveshaft/torsion bar 28' to oscillating rotary movement thereby inhibiting translational movement. A brush head coupler 72 is provided on one end of the driven shaft 52. The brush head coupler 72 is connected to the handle coupler 68 by a simple sliding non-rotatable connection therebetween.

Referring more specifically to FIGS. 9–12, a lower bearing 76 and upper bearing 78 are provided to generally support the driveshaft/torsion bar 28' or driveshaft 29.

Referring now to FIGS. 13–15, the charger base 80 that is used to recharge the batteries of the sonic toothbrush 10 is described. The charger base is formed of ABS in a plurality of injection molded sections. The charger base 80 defines a handle receptacle 84 that is a generally cup shaped portion of the charger base 80. A charging base coil and bobbin 86 is powered to inductively energize the charge coil 58 in the toothbrush 10. A power cord 88 is provided to connect the charger base 80 to a source of alternating current. The charging base coil 86 is energized as indicated by illumination of a charging LED 90. A plurality of extra brush head receptacles 92 may be provided on the top of the charger base 80 so that the toothbrush may be used with several different brush head assemblies 18.

The charger base receives an input voltage of either 110 or 240 volts AC at 50/60 Hz. The charging current is 70 mA+/−15 mA.

Referring now to FIGS. 16–19, the structure of a removable brush head assembly 18 will be described. The brush head assembly 18 includes bristles 14 that are received in a molded brush head 12. The brush head 12 is secured to the driven shaft 52 which is in turn received within the driven shaft holder 54 that is a molded plastic part. A brush head body 94 encloses the driven shaft 52 and driven shaft holder 54 and provides an attractive tapered transition from the brush body housing 16 to the brush head 12. An attachment end 96 is provided on the opposite end of the brush head body 94 from the brush head 12. The brush head assembly 18 is detachably secured to the housing 16 by cooperating locking elements. For example, a first set of locking elements on the attachment end 96 may comprise openings 97 that receive ribs 99, shown in FIG. 12, to provide a detachable connection. Alternatively, a bayonet connection or threaded connection could be used to provide the detachable connection. A color trim ring 98 may be provided on the brush head assembly 18 to facilitate identification of the brush head 12 when the toothbrush 10 is to be used by different persons.

Referring now to FIG. 20, an exemplary circuit diagram for the sonic toothbrush 10 is provided. The toothbrush 10 is controlled by means of an 18-pin OTP processor such as PIC 16LV54R referred to by reference numeral 100. The chip is powered by the rechargeable nickle cadmium batteries by repeatedly pressing the flex switch 24, different levels of amplitude may be obtained from the bobbin coil 40. The power level is indicated by means of the LED board 64. The frequency of the system is controlled by a 1.84 MHZ Abracon frequency oscillator 102. The oscillator controls energizing the clockwise rotation branch 104 and counterclockwise rotation branch 106 that energizes the drive coil to drive the magnets 34 on the magnet plate 32 and thereby cause the torsion bar 28 to twist in alternate an oscillating rotary motion. The electronic circuit uses duty cycle or pulse width modulation to change brushing intensity.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An electric toothbrush comprising:
   a brush head assembly;
   a housing;
   a frame enclosed by the housing;
   a power supply contained within the housing;
   an electric coil and core that is secured relative to the frame and electrically connected to the power supply through a control circuit that creates an alternating flow of current in the coil;
   an elongated driveshaft having a distal end that is connected to the brush head assembly and an internal end that is disposed within the housing;
   a torsion bar clamped by an anchoring plate to the frame at a first end;
   a magnet plate having first and second ends, the magnet plate is connected to one of the torsion bar or the driveshaft;
   at least one magnet arranged on the magnet plate, the magnet being aligned relative to a central axis of the driveshaft, the magnet being located at a radially spaced location relative to the central axis of the shaft, wherein the alternating flow of current in the electric coil at a predetermined frequency causes the first and second ends of the armature magnet plate to be alternately attracted to the coil and core causing the torsion bar to twist and causing the driveshaft to oscillate in an oscillatory rotary motion.

2. The electric toothbrush of claim 1 wherein the frame is a one piece die casting to which the coil torsion bar and a bearing that journals the internal end of the driveshaft are secured.

3. The electric toothbrush of claim 1 wherein a bearing journals the internal end of the elongated shaft for oscillating rotary movement and inhibits translational movement.

4. The electric toothbrush of claim 1 wherein the brush head assembly has a driven shaft that is detachable from the driveshaft.

5. The electric toothbrush of claim 4 wherein the brush head assembly may be detached from the driveshaft without opening the housing and without effecting the coil and magnets.

6. The electric toothbrush of claim 1 wherein said at least one magnet arranged on the magnet plate includes a first magnet and the magnet plate supporting the first and second magnets on a flat plate portion on which the first and second magnets are disposed and a flange extending perpendicularly relative to the flat plate portion, wherein the driveshaft is secured to the flange.

7. The electric toothbrush of claim 1 further comprising a charging coil contained within the housing for recharging the power supply contained in the housing.

8. The electric toothbrush of claim 7 in combination with a charging base, wherein a charging circuit is provided to charge the power supply, and wherein placing the electric toothbrush in the base ends an operating cycle.

9. The electric toothbrush of claim 1 further comprising a single control switch that may be pressed multiple times to select one of a plurality of operational speeds.

10. The electric toothbrush of claim 1 further comprising a plurality of LEDs that indicate at which speed the brush is operating.

11. The electric toothbrush of claim 1 wherein the brush head assembly includes a plurality of bristles having bristle tips that oscillate with the elongated shaft, the bristle tips moving at a speed substantially less than 1.5 meters per second.

12. An electric toothbrush comprising:
a handle enclosing an electric coil that oscillates a driveshaft about a longitudinal axis, the drive shaft is fixedly secured to the handle at a first end by an elongated torsion bar that is coaxial with the driveshaft and clamped by an anchoring plate to the frame at the first end, the driveshaft is received in a bearing disposed in the handle at a second end of the driveshaft that oscillates in an oscillatory rotary motion relative to the handle; and
a frame that is formed as a one piece die casting to which the coil, torsion bar and a bearing that journals the internal end of the driveshaft are secured; and
a brush head assembly removably secured to the handle, the brush head assembly having a driven shaft that is operatively secured to the second end of the driveshaft to oscillate with the driveshaft.

13. The electric toothbrush of claim 12 wherein a bearing journals the internal end of the driveshaft for oscillating rotary movement and inhibits translational movement.

14. The electric toothbrush of claim 12 wherein the brush head assembly has a driven shaft that is detachable from the driveshaft.

15. The electric toothbrush of claim 12 wherein the brush head assembly may be detached from the driveshaft without opening the housing and without effecting the coil, core, and magnets.

16. The electric toothbrush of claim 12 further comprising a magnet plate supporting the first and second magnets, the magnet plate having a flat plate portion on which the first and second magnets are secured and a flange extending perpendicularly relative to the flat plate portion, wherein the driveshaft is secured to the flange.

17. The electric toothbrush of claim 12 further comprising a charging coil contained within the housing for recharging the batteries contained in the housing.

18. The electric toothbrush of claim 17 in combination with a charging base, wherein a charging circuit is provided to charge the batteries, and wherein placing the electric toothbrush in the base ends an operating cycle.

19. The electric toothbrush of claim 12 further comprising a single control switch that may be pressed multiple times to select one of a plurality of operational speeds.

20. The electric toothbrush of claim 12 further comprising a plurality of LEDs that indicate the speed at which the brush is operating.

21. The electric toothbrush of claim 12 wherein the brush head assembly includes a plurality of bristles having bristle tips that oscillate with the elongated shaft, the bristle tips moving at less than 1.4 meters per second.

22. An electric toothbrush comprising:
a brush head assembly;
a housing;
a frame enclosed by the housing;
a power supply contained within the housing;
an electric coil and core that is secured relative to the frame and electrically connected to the power supply through a control circuit that creates an alternating flow of current in the coil;
an elongated driveshaft having a distal end that is connected to the brush head assembly and an internal end that is disposed within the housing;
a torsion bar is secured to the frame at a first end;
a magnet plate having first and second ends, the magnet plate is connected to one of the torsion bar or the driveshaft;
at least one magnet arranged on the magnet plate, the magnet being aligned relative to a central axis of the driveshaft, the magnet being located at a radially spaced location relative to the central axis of the shaft, wherein the alternating flow of current in the electric coil at a predetermined frequency causes the first and second ends of the magnet plate to be alternately attracted to the coil and core causing the torsion bar to twist and causing the driveshaft to oscillate in an oscillatory rotary motion, wherein said at least one magnet arranged on the magnet plate includes a first magnet and a second magnet, and wherein the torsion bar is secured to the magnet plate between the first and second magnets and the driveshaft is connected at the internal end thereof to the magnet plate.

23. An electric toothbrush comprising:
a handle enclosing an electric coil that oscillates a driveshaft about a longitudinal axis, the drive shaft is fixedly secured to the handle at a first end by an elongated torsion bar that is coaxial with the driveshaft and secured to a magnet plate between a first magnet and a second magnet, the driveshaft connected at an internal end thereof to the magnet plate, the driveshaft is received in a bearing disposed in the handle at a second end of the driveshaft that oscillates in an oscillatory rotary motion relative to the handle; and
a brush head assembly removably secured to the handle, the brush head assembly having a driven shaft that is operatively secured to the second end of the driveshaft to oscillate with the driveshaft.

* * * * *

UNITED STATES PATENT AND TRADEMARK OFFICE
CERTIFICATE OF CORRECTION

PATENT NO. : 6,760,945 B2 Page 1 of 1
DATED : July 13, 2004
INVENTOR(S) : Roman S. Ferber et al.

It is certified that error appears in the above-identified patent and that said Letters Patent is hereby corrected as shown below:

<u>Column 6,</u>
Line 57, delete "armature".
Line 62, insert a comma -- , -- after "coil".

<u>Column 7,</u>
Line 41, delete "and".

Signed and Sealed this

Thirtieth Day of November, 2004

JON W. DUDAS
*Director of the United States Patent and Trademark Office*